US008853472B2

(12) United States Patent
Nappa et al.

(10) Patent No.: US 8,853,472 B2
(45) Date of Patent: Oct. 7, 2014

(54) PROCESSES FOR REDUCING THE AMOUNT OF MONOFLUOROACETATE IN HYDROFLUOROOLEFIN PRODUCTION

(75) Inventors: Mario Joseph Nappa, Newark, DE (US); Patricia Cheung, Glen Mills, PA (US); Karl R. Krause, Kennett Square, PA (US); Michael A. Sisk, Hockessin, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 50 days.

(21) Appl. No.: 13/318,557

(22) PCT Filed: May 7, 2010

(86) PCT No.: PCT/US2010/033991
§ 371 (c)(1),
(2), (4) Date: Nov. 2, 2011

(87) PCT Pub. No.: WO2010/129844
PCT Pub. Date: Nov. 11, 2010

(65) Prior Publication Data
US 2012/0046505 A1    Feb. 23, 2012

Related U.S. Application Data

(60) Provisional application No. 61/176,500, filed on May 8, 2009.

(51) Int. Cl.
C07C 17/38 (2006.01)
C07C 17/25 (2006.01)
(52) U.S. Cl.
CPC ..................... C07C 17/25 (2013.01)
USPC ........................................... 570/177
(58) Field of Classification Search
CPC ........................................ C07C 17/38
USPC ........................................ 570/177
See application file for complete search history.

(56) References Cited

U.S. PATENT DOCUMENTS

| | | | | |
|---|---|---|---|---|
| 2,365,898 A * | 12/1944 | Morris et al. | ................ | 208/240 |
| 4,560,759 A | 12/1985 | Hiratani | | |
| 6,548,719 B1 | 4/2003 | Nair et al. | | |
| 7,230,146 B2 | 6/2007 | Merkel | | |
| 2010/0121115 A1 | 5/2010 | Rao et al. | | |

FOREIGN PATENT DOCUMENTS

| | | | | |
|---|---|---|---|---|
| GB | WO 2008/075017 A2 * | 6/2008 | ............. | C07C 21/18 |
| WO | 2008030439 A2 | 3/2008 | | |
| WO | 2008030440 A3 | 3/2008 | | |
| WO | 2008075017 A2 | 6/2008 | | |
| WO | WO 2008075017 A2 * | 6/2008 | | |
| WO | 2008147835 A1 | 12/2008 | | |

OTHER PUBLICATIONS

PCT/US2010/033991, International Search Report, Aug. 26, 2010, Sylvia Lampreia.
Salsbury et al. Analytical Chemistry, vol. 23 No. 4, Apr. 1951, pp. 603-608.
Saunders, B.C. (1972) Chemical Characteristics of the Carbon-Fluorine Bond. in "Carbon-Fluorine Compounds: Chemistry, Biochemistry and Biological Activities", pp. 9-32, Elsevier, New York.

* cited by examiner

*Primary Examiner* — Sudhakar Katakam
*Assistant Examiner* — Kofi Adzamli

(57) ABSTRACT

A process is disclosed for reducing the amount of monofluoroacetate. The process involves (a) contacting a hydrofluorocarbon with a reactant basic aqueous solution to produce an organic phase solution containing a hydrofluoroolefin and an aqueous phase solution containing a monofluoroacetate; and (b) heating the aqueous phase solution to an effective temperature to reduce the amount of monofluoroacetate in the aqueous phase solution, wherein fluoride concentration in the aqueous phase solution is substantially high. Another process is disclosed for reducing the amount of monofluoroacetate. The process involves (a) contacting a first batch of hydrofluorocarbon with a first batch of reactant basic aqueous solution to produce a first batch of organic phase solution containing a hydrofluoroolefin and a first batch of aqueous phase solution containing a monofluoroacetate; (b) separating the first batch of organic phase solution from the first batch of aqueous phase solution; (c) mixing a second batch of hydrofluorocarbon and a second batch of reactant basic aqueous solution with the separated first batch of organic phase solution to produce a second batch of organic phase solution containing a hydrofluoroolefin and a second batch of aqueous phase solution containing a monofluoroacetate; (d) combining the first batch of aqueous phase solution with the second batch of aqueous phase solution; and (e) heating the combined aqueous phase solutions to an effective temperature to reduce the amount of monofluoroacetate in the combined aqueous phase solutions, wherein fluoride concentration in the combined aqueous phase solutions is substantially high.

22 Claims, No Drawings

US 8,853,472 B2

PROCESSES FOR REDUCING THE AMOUNT OF MONOFLUOROACETATE IN HYDROFLUOROOLEFIN PRODUCTION

BACKGROUND

1. Field of the Disclosure

This disclosure relates in general to processes for producing hydrofluorocarbons. In particular, this disclosure relates to processes for reducing the amount of monofluoroacetate generated in the processes used to produce hydrofluoroolefins.

2. Description of Related Art

The refrigeration industry has been working for the past few decades to find replacement refrigerants for the ozone depleting chlorofluorocarbons (CFCs) and hydrochlorofluorocarbons (HCFCs) being phased out as a result of the Montreal Protocol. The solution for most refrigerant producers has been the commercialization of hydrofluorocarbon (HFC) refrigerants. The new HFC refrigerants, have zero ozone depletion potential and thus are not affected by the current regulatory phase-out as a result of the Montreal Protocol.

BRIEF SUMMARY OF THE DISCLOSURE

The present disclosure provides a process for reducing the amount of monofluoroacetate. The process comprises (a) contacting a hydrofluorocarbon with a reactant basic aqueous solution to produce an organic phase solution comprising a hydrofluoroolefin and an aqueous phase solution comprising a monofluoroacetate; and (b) heating said aqueous phase solution to an effective temperature to reduce the amount of monofluoroacetate in said aqueous phase solution, wherein fluoride concentration in said aqueous phase solution is substantially high.

The present disclosure provides another process for reducing the amount of monofluoroacetate. The process comprises: (a) contacting a first batch of hydrofluorocarbon with a first batch of reactant basic aqueous solution to produce a first batch of organic phase solution comprising a hydrofluoroolefin and a first batch of aqueous phase solution comprising a monofluoroacetate; (b) separating said first batch of organic phase solution from said first batch of aqueous phase solution; (c) mixing a second batch of hydrofluorocarbon and a second batch of reactant basic aqueous solution with said separated first batch of organic phase solution to produce a second batch of organic phase solution comprising a hydrofluoroolefin and a second batch of aqueous phase solution comprising a monofluoroacetate; (d) combining said first batch of aqueous phase solution with said second batch of aqueous phase solution; and (e) heating said combined aqueous phase solutions to an effective temperature to reduce the amount of monofluoroacetate in said combined aqueous phase solutions, wherein fluoride concentration in said combined aqueous phase solutions is substantially high.

DETAILED DESCRIPTION

In addition to ozone depleting concerns, global warming is another environmental concern. Thus, there is a need for heat transfer compositions that have not only low ozone depletion potentials, but also low global warming potentials. Certain hydrofluoroolefins (HFOs) are believed to meet both goals. However, their production contains many unforeseen problems, particularly concerning side reactions and the presence of deleterious byproducts.

The foregoing general description and the following detailed description are exemplary and explanatory only and are not restrictive of the invention, as defined in the appended claims. Other features and benefits of any one or more of the embodiments will be apparent from the following detailed description, and from the claims.

The term "reactant basic aqueous solution", as used herein, means the basic aqueous solution used as a starting material in a hydrofluorocarbon's dehydrofluorination reaction.

The term "dehydrofluorination", as used herein, means a process during which hydrogen and fluorine on adjacent carbons in a molecule are removed.

The term "hydrofluorocarbon", as used herein, means a molecule containing hydrogen, fluorine and at least two carbons.

The term "hydrofluoroolefin", as used herein, means a molecule containing hydrogen, carbon, fluorine, and at least one carbon-carbon double bond.

The term "monofluoroacetate", as used herein, means a salt of a monofluoroacetic acid which can be represented by the general formula of $(FCH_2COO^-)_n M^{n+}$, wherein n is an integer. Examples of monofluoroacetate include $FCH_2COOK$ (potassium monofluoroacetate, KMFA), $FCH_2COONa$ (sodium monofluoroacetate), $(FCH_2COO)_2Ca$, $FCH_2COONH_4$, and $FCH_2COONR_4$, wherein each R is independently hydrogen, a $C_1$ to $C_{16}$ alkyl group, aralkyl group, or substituted alkyl group, provided that not all R are hydrogens.

The term "fluoride concentration", as used herein, means the total weight of fluoride in the product basic aqueous solution divided by the total weight of the product basic aqueous solution.

The term "alkyl", as used herein, includes cyclic or acyclic and straight-chain or branched alkyl groups, such as, methyl, ethyl, n-propyl, propyl, or the different isomers thereof.

The term "aralkyl", as used herein, means an alkyl group wherein one or more hydrogens on carbon atoms have been substituted by an aryl group. Examples of an aralkyl group include $C_6H_5CH_2$—.

The term "substituted alkyl group", as used herein, means an alkyl group wherein one or more hydrogens on carbon atoms have been substituted by functional groups, such as hydroxyl groups, halogens, et al., other than aryl groups.

The term "ppmw", as used herein, means parts-per-million-by-weight.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true for present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

Disclosed is a process for reducing the amount of monofluoroacetate produced during the synthesis of a hydrofluoroolefin. The process comprises (a) contacting a hydrofluorocarbon with a reactant basic aqueous solution to produce an organic phase solution comprising a hydrofluoroolefin and an aqueous phase solution comprising a monofluoroacetate; and (b) heating said aqueous phase solution to an effective temperature to reduce the amount of monofluoroacetate in said aqueous phase solution, wherein fluoride concentration in said aqueous phase solution is substantially high.

A hydrofluoroolefin may be produced by a dehydrofluorination reaction by contacting a hydrofluorocarbon with a reactant basic aqueous solution. It was found by the inventors that the resulting aqueous phase solution may contain monofluoroacetate. Since monofluoroacetate is toxic, it is desirable to reduce its amount in the aqueous phase solution.

In some embodiments of this invention, monofluoroacetate is $FCH_2COOK$, $FCH_2COONa$, or mixtures thereof.

In this disclosure, a hydrofluorocarbon is contacted with a reactant basic aqueous solution under suitable conditions to produce a hydrofluoroolefin through a dehydrofluorination process. It was found that small amounts of monofluoroacetate might also be generated by contacting a hydrofluorocarbon with a reactant basic aqueous solution. Typically, two separate phases, i.e., an organic phase and an aqueous phase, are formed when a hydrofluorocarbon is contacted with a reactant basic aqueous solution. The contents of these two phases constantly change as the dehydrofluorination reaction proceeds. Typically, at the beginning of the dehydrofluorination reaction, the organic phase solution primarily comprises hydrofluorocarbon starting materials and, optionally, organic solvents, while the aqueous phase solution primarily comprises reactant basic aqueous solutions and, optionally, some hydrophilic organic solvents such as alcohols. Near the end of the dehydrofluorination reaction, typically, the organic phase solution primarily comprises hydrofluoroolefin products, residual hydrofluorocarbon starting materials and optionally organic solvents, while the aqueous phase solution primarily comprises residual or extra bases from the reactant basic aqueous solutions, fluorides, water, small amounts of monofluoroacetate and optionally some hydrophilic organic solvents such as alcohols. A phase transfer catalyst may also be present in either or both phases.

In some embodiments of this invention, the organic phase and the aqueous phase are uniform without separate layers in each of them. In other embodiments of this invention, the organic phase and/or the aqueous phase are not uniform. Two or more immiscible layers can exist in the organic phase and/or the aqueous phase.

Examples of hydrofluorocarbons in this disclosure include hydrofluoropropanes, hydrofluorobutanes and hydrofluoropentanes. In some embodiments of this invention, a hydrofluorocarbon is contacted with a reactant basic aqueous solution to produce an organic phase solution comprising a hydrofluoropropene and an aqueous phase sol on comprising a monofluoroacetate.

In some embodiments of this invention, 1,1,1,2,3-pentafluoropropane ($CF_3CHFCH_2F$, HFC-245eb) is contacted with a reactant basic aqueous solution to produce an organic phase solution comprising 2,3,3,3-tetrafluoro-1-propene ($CF_3CF=CH_2$, HFO-1234yf) and an aqueous phase solution comprising a monofluoroacetate.

In some embodiments of this invention, 1,1,1,2,3,3-hexafluoropropane ($CF_3CHFCHF_2$, HFC-236ea) is contacted with a reactant basic aqueous solution to produce an organic phase solution comprising 1,2,3,3,3-pentafluoro-1-propene ($CF_3CF=CHF$, HFO-1225ye) and an aqueous phase solution comprising a monofluoroacetate. HFO-1225ye may exist as two configurational isomers, E, or Z. HFO-1225ye as used herein refers to the isomers, E-HFO-1225ye or Z-HFO-1225ye, as well as any combinations or mixtures of such isomers.

In some embodiments of this invention, 1,1,1,3,3-pentafluoropropane ($CF_3CH_2CHF_2$, HFC-245fa) is contacted with a reactant basic aqueous solution to produce an organic phase solution comprising 1,3,3,3-tetrafluoropropene ($CF_3CH=CHF$, HFO-1234ze) and an aqueous phase solution comprising a monofluoroacetate. HFO-1234ze may exist as two configurational isomers, E, or Z. HFO-1234ze as used herein refers to the isomers. E-HFO-1234ze or Z-HFO-1234ze, as well as any combinations or mixtures of such isomers.

As used herein, the reactant basic aqueous solution is a liquid that is primarily an aqueous liquid having a pH of over 7; the liquid may be a solution, dispersion, emulsion, suspension or the like. In some embodiments of this invention, the reactant basic aqueous solution has a pH of 8 OF higher. In some embodiments of this invention, the reactant basic aqueous solution has a pH of 10 or higher. In some embodiments of this invention, the reactant basic aqueous solution has a pH of between 10 and 13. In some embodiments of this invention, the reactant basic aqueous solution contains small amounts of organic solvents which may be miscible or immiscible with water. In some embodiments of this invention, the liquid medium in the reactant basic aqueous solution is at least 55 wt % (weight percent) of water. In some embodiments of this invention, the water is tap water. In some embodiments of this invention, the water is deionized water or distilled water.

In some embodiments of this invention, an inorganic base is used to form the reactant basic aqueous solution. Such inorganic base can be selected from the group consisting of hydroxide, oxide, carbonate, and phosphate salts of alkali, alkaline earth metals and mixtures thereof. In some embodiments, such inorganic base can be selected from the group consisting of lithium hydroxide, sodium hydroxide, potassium hydroxide, calcium hydroxide, calcium oxide, sodium carbonate, potassium carbonate, sodium phosphate, potassium phosphate, ammonium hydroxide and mixtures thereof. In some embodiments, such inorganic base is sodium hydroxide, potassium hydroxide, or mixtures thereof.

In some embodiments of this invention, the reactant basic aqueous solution is an aqueous solution of a quaternary ammonium hydroxide of the formula $NR_4OH$ wherein each R is independently hydrogen, a $C_1$ to $C_{16}$ alkyl group, aralkyl group, or substituted alkyl group, provided that not all R are hydrogens. Examples of $NR_4OH$ compounds useful in this invention are tetra-n-butylammonium hydroxide, tetra-n-propylammonium hydroxide, tetraethylammonium hydroxide, tetramethylammonium hydroxide, benzyltrimethylammonium hydroxide, hexadecyltrimethyammonium hydroxide, and choline hydroxide.

The amount of base in the reactant basic aqueous solution required to convert by dehydrofluorination a hydrofluorocarbon to a hydrofluoroolefin is approximately the stoichiometric quantity or about 1 mole of base to one mole of hydrofluorocarbon. In some embodiments of this invention, it may be desirable to employ a ratio of base (in the reactant basic aqueous solution) to hydrofluorocarbon of greater than one; for example, this ratio could be desirable as a way to increase the reaction rate In some embodiments, large excesses of base (in the reactant basic aqueous solution) can be used. In some embodiments, an amount of base (in the reactant basic aqueous solution) that is slightly below stoichiometric may be employed.

In this disclosure, the hydrofluorocarbon is contacted with the reactant basic aqueous solution within a temperature range at which the hydrofluorocarbon will dehydrofluorinate. In some embodiments of this invention, such temperatures can be from about 5° C. to about 150° C. In some embodiments of this invention, the hydrofluorocarbon is contacted with the reactant basic aqueous solution at a temperature of from about 10° C. to about 100° C. In some embodiments of this invention, the hydrofluorocarbon is contacted with the reactant basic aqueous solution at a temperature of from about 20° C. to about 60° C. Pressure is not critical to the dehydrofluorination reactions in this disclosure. The hydrofluorocarbon can be contacted with the reactant basic aqueous solution at atmospheric pressure, super-atmospheric pressure, or under reduced pressure. In some embodiments of this invention, the hydrofluorocarbon is contacted with the reactant basic aqueous solution at atmospheric pressure.

Optionally, the hydrofluorocarbon is contacted with the reactant basic aqueous solution in the presence of an organic solvent. In some embodiments of this invention, the organic solvent is selected from the group consisting of benzene and its derivatives, alcohols, alkyl and aryl halides, alkyl and aryl nitriles, alkyl, alkoxy and aryl ethers, amides, ketones, sulfoxides, phosphate esters and mixtures thereof.

In some embodiments of this invention, the organic solvent is selected from the group consisting of toluene, methanol, ethanol, proponal, isopropanol, 2-methyl-2-propanol (tert-butanol), di(ethylene glycol), dichloromethane, chloroform, carbon tetrachloride, acetonitrile, propionitrile, butyronitrile, methyl glutaronitrile, adiponitrile, benzonitrile, ethylene carbonate, propylene carbonate, methyl ethyl ketone, methyl isoamyl ketone, diisobutyl ketone, anisole, 2-methyltetrahydrofuran, tetrahydrofuran (THF), dioxane, diglyme, triglyme, tetraglyme, N,N-dimethyl formamide, N,N-dimethyl acetamide, N-methyl pyrrolidinone, sulfolane, dimethyl sulfoxide, perfluoro-N-methyl morpholine, perfluorotetrahydrofuran, and mixtures thereof. In some embodiments of this invention, the organic solvent is selected from the group consisting of toluene, ethanol, isopropanol, 2-methyl-2-propanol (tert-butanol), di(ethylene glycol), dichloromethane, carbon tetrachloride, acetonitrile, adiponitrile, 2-methyl tetrahydrofuran, tetrahydrofuran, dioxane, diglyme, tetraglyme, and mixtures thereof. In some embodiments of this invention, the organic solvent is THF.

Optionally, the hydrofluorocarbon is contacted with the reactant basic aqueous solution in the presence of a phase transfer catalyst. As used herein, a phase transfer catalyst is intended to mean a substance that facilitates the transfer of ionic compounds into an organic phase from an aqueous phase or from a solid phase. The phase transfer catalyst facilitates the reaction between water-soluble and water-insoluble reaction components. While various phase transfer catalysts may function in different ways, their mechanism of action is not determinative of their utility in the present invention provided that the phase transfer catalyst facilitates the dehydrofluorination reaction.

In some embodiments of this invention, the phase transfer catalyst is selected from the group consisting of crown ethers, onium salts, cryptands, polyalkylene glycols, and mixtures and derivatives thereof. The phase transfer catalyst can be ionic or neutral.

As used herein, cryptands are any of a family of bi- and polycyclic multidentate ligands for a variety of cations formed by joining bridgehead structures with chains that contain properly spaced donor atoms. For example, bicyclic molecules that result from joining nitrogen bridgeheads with chains of (—OCH$_2$CH$_2$—) groups as in 2.2.2-cryptand (4,7,13,16,21,24-hexaoxa-1,10-diazabicyclo-(8.8.8)hexacosane) is available under the brand names Cryptand™ 222 and Kryptofix™ 222. The donor atoms of the bridges may all be O, N, or S, or the compounds may be mixed donor macrocycles in which the bridge strands contain combinations of different donor atoms.

Crown ethers are cyclic molecules in which ether groups are connected by dimethylene linkages; the compounds form a molecular structure that is believed to be capable of "receiving" or holding the alkali metal ion of the hydroxide and to thereby facilitate the reaction. In some embodiments of this invention, it is preferred to match crown ether phase transfer catalysts with certain bases used in the basic aqueous solutions. In some embodiments of this invention, crown ether 18-crown-6 is used in combination with potassium hydroxide basic aqueous solution; 15-crown-5 is used in combination with sodium hydroxide basic aqueous solution; 12-crown-4 is used in combination with lithium hydroxide basic aqueous solution. Derivatives of the above crown ethers are also useful, e.g., dibenzo-18-crown-6, dicyclohexano-18-crown-6, dibenzo-24-crown-8 and dibenzo-12-crown-4. Other polyethers particularly useful in combination with basic aqueous solution made from alkali metal compounds, and especially for lithium, are described in U.S. Pat. No. 4,560,759 the disclosure of which is herein incorporated by reference.

In some embodiments of this invention, onium salts include quaternary phosphonium salts and quaternary ammonium salts that may be used as the phase transfer catalyst in the dehydrofluorination processes of the present invention; such compounds can be represented by formulas I and II:

$$R^1 R^2 R^3 R^4 P^{(+)} X^{(-)} \quad \text{(I)}$$

$$R^1 R^2 R^3 R^4 N^{(+)} X^{(-)} \quad \text{(II)}$$

wherein each of $R^1$, $R^2$, $R^3$ and $R^4$, which may be the same or different, is an alkyl group, an aryl group, an aralkyl group or a substituted alkyl group, and X is selected from the group consisting of F, Cl, Br, I, OH, CO$_3$, HCO$_3$, SO$_4$, HSO$_4$, H$_2$PO$_4$, HPO$_4$ and PO$_4$. Specific examples of these compounds include tetra-n-butylammonium hydroxide, tetramethylammonium chloride, tetramethylammonium bromide, benzyltriethylammonium chloride, methyltri-n-octylammonium chloride (also known as Aliquat™ 336), dodecyltrimethylammonium bromide, tetra-n-butylammonium chloride, tetra-n-butylammonium bromide, tetra-n-butylammonium hydrogen sulfate, tetra-n-butylphosphonium chloride, tetraphenylphosphonium bromide, tetraphenylphosphonium chloride, triphenylmethylphosphonium bromide and triphenylmethylphosphonium chloride. In one embodiment of this invention, benzyltriethylamrnonium chloride is used under strongly basic conditions. Other useful compounds within this class of compounds include those exhibiting high temperature stabilities (e.g., up to about 200° C.) including 4-dialkylaminopyridinium salts, tetraphenylarsonium chloride, bis[tris(dimethylamino)phosphine]iminium chloride, and tetratris[tris(dimethylamino)phosphinimino]phosphonium chloride. In some embodiments of this invention, the phase transfer catalyst is methyltri-n-octylammonium chloride, tetra-n-butylammonium chloride, tetra-n-butylammonium bromide, tetra-n-butylammonium hydroxide, or their mixtures. In some embodiments of this invention, the phase transfer catalyst is methyltri-n-octylammonium chloride, tetra-n-butylammonium bromide, or mixtures thereof.

In some embodiments of this invention, polyalkylene glycols and their ether derivatives are useful as phase transfer catalysts. In some embodiments of this invention, the polyalkylene glycols and their ether derivatives can be represented by the formula:

wherein $R^5$ is an alkylene group containing two or more carbons, each of $R^6$ and $R^7$, which may be the same or different, is a hydrogen atom, an alkyl group, an aryl group, or an aralkyl group, and t is an integer of at least 2. Such compounds include, for example, glycols such as diethylene glycol, triethylene glycol, tetraethylene glycol, pentaethylene glycol, hexaethylene glycol, diisopropylene glycol, dipropylene glycol, tripropylene glycol, tetrapropylene glycol and tetramethylene glycol, and their monoalkyl ethers such as monomethyl, monoethyl, monopropyl and monobutyl ethers of such glycols, and phenyl ethers of such glycols, benzyl ethers of such glycols, and dialkyl ethers such as tetraethylene glycol dimethyl ether and pentaethylene glycol dimethyl ether, and polyalkylene glycol ethers such as polyethylene glycol (average molecular weight about 300) dimethyl ether, polyethylene glycol (average molecular weight about 300) dibutyl ether, and polyethylene glycol (average molecular weight about 400) dimethyl ether.

Mixtures of the above described phase transfer catalysts from within one of the groups may also be useful as well as mixtures of two or more phase transfer catalysts selected from different groups. Examples of these mixtures include crown ethers and onium salts, quaternary phosphonium salts and quaternary ammonium salts, and crown ethers and polyalkylene glycol ethers.

The process of contacting a hydrofluorocarbon with a reactant basic aqueous solution may be carried out by adding the reactant basic aqueous solution to the hydrofluorocarbon starting material or by adding the hydrofluorocarbon starting material to the reactant basic aqueous solution. Accordingly, in some embodiments of this invention, the reactant basic aqueous solution is added to the hydrofluorocarbon starting material optionally in the presence of an organic solvent and optionally in the presence of a phase transfer catalyst. In other embodiments of this invention, the hydrofluorocarbon starting material, optionally dissolved in an organic solvent, is added to the reactant basic aqueous solution optionally in the presence of a phase transfser catalyst and optionally in the presence of an organic solvent.

In some embodiments of this invention, the process of contacting the hydrofluorocarbon with the reactant basic aqueous solution is carried out in batch techniques. In some embodiments of this invention, the contacting process is carried out in continuous mode of operation.

In some embodiments of this invention, in the batch mode, the reactant basic aqueous solution, hydrofluorocarbon, optionally organic solvent, and optionally phase transfer catalyst are combined in a suitable vessel for a time sufficient to convert at least a portion of the hydrofluorocarbon to hydrofluoroolefin and then the hydrofluoroolefin is recovered from the reaction mixture.

In some embodiments of this invention, in a continuous mode of operation, the reaction vessel is charged with the reactant basic aqueous solution, optionally organic solvent, and optionally phase transfer catalyst and the hydrofluorocarbon is fed to the reactor. The reaction vessel is fitted with a condenser cooled to a temperature sufficient to reflux the hydrofluorocarbon, but permit the hydrofluoroolefin to exit the reaction vessel and collect in an appropriate vessel such as cold trap.

In some embodiments of this invention, the process of contacting the hydrofluorocarbon with the reactant basic aqueous solution may be carried out at such a combination of temperature and pressure as to permit the recovery of the hydrofluoroolefin product by distillation either during or after the reaction. Suitable combinations of temperature and pressure may be readily deduced from the physical properties of the starting material and product by those skilled in the art.

In some embodiments of this invention, the hydrofluoroolefin product of the dehydrofluorination reaction may be collected by decanting the organic phase solution and isolating the hydrofluoroolefin product by washing the organic phase solution with water or by distilling the organic phase solution. Further purification may be accomplished by distillation employing techniques well-known in the art.

In some embodiments of this invention, the aqueous phase solution is separated from the organic phase solution before heated to reduce the amount of monofluoroacetate. The separation can be achieved by various methods including decantation and distillation.

In some embodiments of this invention, the aqueous phase solution is further treated before being heated to reduce the amount of monofluoroacetate. For example, additional base, either same or different from the one used in the reactant basic aqueous solution, may be added to the aqueous phase solution. In some embodiments of this invention, before or during the heating process to reduce the amount of monofluoroacetate, the aqueous phase solution can be distilled to collect the hydrofluorocarbon, hydrofluoroolefin and/or organic solvents.

As used herein, the aqueous phase solution is an aqueous liquid in the form of either a solution, dispersion, emulsion, suspension, or the like. As described above, the content of the aqueous phase solution may change as the dehydrofluorination reaction proceeds. The content of the aqueous phase solution may also change due to some side-reactions, change of conditions (e.g., temperature, pressure), or some treatments of the aqueous phase solution as described above.

In this disclosure, the aqueous phase solution is heated to an effective temperature to reduce the amount of monofluoroacetate in the aqueous phase solution, wherein fluoride concentration in the aqueous phase solution is substantially high.

In some embodiments of this invention, the aqueous phase solution is heated to a temperature of from about 80° C. to about 300° C. to reduce the amount of monofluoroacetate. In some embodiments of this invention, the aqueous phase solution is heated to a temperature of from about 100° C. to about 225° C. to reduce the amount of monofluoroacetate. In some embodiments of this invention, the aqueous phase solution is heated to a temperature of from about 125° C. to about 200° C. to reduce the amount of monofluoroacetate. In the processes of reducing the amount of monofluoroacetate, in some embodiments, a substantially high fluoride concentration in the aqueous phase solution is at least 0.5 wt %; in some embodiments, fluoride concentration in the aqueous phase solution is at least 5 wt %; in some embodiments, fluoride concentration in the aqueous phase solution is at least 12 wt %.

In the processes of reducing the amount of monofluoroacetate, in some embodiments, the aqueous phase solution has a pH of over 7. In some embodiments, during such processes, the aqueous phase solution has a pH of over 8. In some embodiments, during such processes, the aqueous phase solution has a pH of over 10. In some embodiments, during such processes, the aqueous phase solution has a pH of 10-14.

In some embodiments of this invention, the total amount of monofluoroacetate in the aqueous phase solution is reduced to less than about 10 ppmw. In some embodiments of this invention, the total amount of monofluoroacetate in the aqueous phase solution is reduced to less than about 5 ppmw. In some embodiments of this invention, the total amount of monofluoroacetate in the aqueous phase solution is reduced to less than about 0.5 ppmw.

The pressure in the process of reducing the amount of monofluoroacetate is not critical. The process can be conducted at atmospheric pressure, super-atmospheric pressure, or under reduced pressure. In some embodiments of this invention, the process of reducing the amount of monofluoroacetate is carried out under autogenous pressure.

Typically, the monofluoroacetate reduction process rate is higher at higher temperatures. Typically, it takes several minutes to several days to reduce the amount of monofluoroacetate in the aqueous phase solution to the sufficient low level.

Disclosed is another process for reducing the amount of monofluoroacetate. The process comprises: (a) contacting a first batch of hydrofluorocarbon with a first batch of reactant basic aqueous solution to produce a first batch of organic phase solution comprising a hydrofluoroolefin and a first batch of aqueous phase solution comprising a monofluoroacetate; (b) separating said first batch of organic phase solution from said first batch of aqueous phase solution; (c) mixing a second batch of hydrofluorocarbon and a second batch of reactant basic aqueous solution with said separated first batch of organic phase solution to produce a second batch of organic phase solution comprising a hydrofluoroolefin and a second batch of aqueous phase solution comprising a monofluoroacetate; (d) combining said first batch of aqueous phase solution with said second batch of aqueous phase solution; and (e) heating said combined aqueous phase solutions to an effective temperature to reduce the amount of monofluoroacetate in said combined aqueous phase solutions, wherein fluoride concentration in said combined aqueous phase solutions is substantially high In some embodiments of this invention, during or at the end of the first batch of dehydrofluorination reaction, the resulting first batch of organic phase solution can be separated from the first batch of aqueous phase solution and reused to mix with the second batch of reactant basic aqueous solution and the second batch of hydrofluorocarbon for the second batch of dehydrofluorination reaction. The dehydrofluorination reactions can be conducted by the techniques described above. The separation can be achieved by various methods including decantation and distillation. Optionally, additional organic solvents and/or phase transfer catalysts may be added to the second batch of dehydrofluorination reaction mixture. In some embodiments of this invention, the second batch of hydrofluorocarbon is the same as the one of the first batch. In some embodiments of this invention, the base used to form the second batch of reactant basic aqueous solution is the same as the one used in the first batch.

The second batch of aqueous phase solution can be separated from the second batch of organic phase solution and combined with the first batch of aqueous phase solution. The separation can be achieved by various methods including decantation and distillation. The combined aqueous phase solutions can be heated to reduce the amount of monofluoroacetate in the combined aqueous phase solutions according to the techniques described above.

The method of reusing the previous batch of organic phase solution in the subsequent batch of dehydrofluorination reaction processes can be repeated indefinitely, i.e., the second batch of organic phase solution can be separated during or at the end of the second batch of dehydrofluorination reaction and reused for the third batch of dehydrofluorination reaction process, and so on. The aqueous phase solutions resulting from the first, second and subsequent batchs of dehydrofluorination reaction processes can be combined and heated to reduce the amount of monofluoroacetate.

The reactors, distillation columns, and their associated feed lines, effluent lines, and associated units used in applying the processes of embodiments of this invention should be constructed of materials resistant to corrosion. Typical materials of construction include stainless steels, in particular of the austenitic type, the well-known high nickel alloys, such as Monel™ nickel-copper alloys, Hastelloy™ nickel-based alloys and, Inconel™ nickel-chromium alloys, and copper-clad steel. Alternatively, the processes of embodiments of this invention may be carried out in fluoropolymer-lined metal reactors.

Many aspects and embodiments have been described above and are merely exemplary and not limiting. After reading this specification, skilled artisans appreciate that other aspects and embodiments are possible without departing from the scope of the invention.

EXAMPLES

The concepts described herein will be further described in the following examples, which do not limit the scope of the invention described in the claims.

Example 1

Example 1 demonstrates that monofluoroacetate is generated in the dehydrofluorination process of HFC-245eb, and its amount can be reduced in a basic aqueous solution at an elevated temperature in the presence of substantially high fluoride concentration. Example 1 also demonstrates that the organic phase solutions from previous batchs of dehydrofluorination reactions can be reused in the subsequent batch of dehydrofluorination reaction.

About 1065 pounds (lbs) of HFC-245eb was fed at room temperature to an agitated reactor containing 300 lbs of THF, 6 lbs of tetra-n-butylammonium bromide, and 1100 lbs of 45 wt % KOH aqueous solution. After feeding 100 lbs of HFC-245eb, the effluent was found to contain 95.5 mol % (molar percent) HFO-1234yf. At the end of the run the aqueous phase solution was separated and found to contain 52.3 ppmw of potassium monofluoroacetate by ion chromatography/mass spectrometry (ICMS). At the end of the run, the aqueous phase solution was decanted.

Another batch of 1100 lbs of 45 wt % KOH aqueous solution was added to the organic phase solution from above and another 1065 lbs of HFC-245eb was added at room temperature while agitating. The effluent of the reactor after 142 lbs of HFC-245eb had been fed was found to contain 97.5 mol % HFO-1234yf. The aqueous phase solution was separated, analyzed and found to contain 89.9 ppmw of KMFA. The aqueous phase solutions from both runs above were combined and heated to 150° C. for 72 hours and then reanalyzed by ICMS and KMFA was non-detectable (i.e., having a concentration lower than 1 ppmw).

Example 2

Example 2 demonstrates that monofluoroacetate is generated in the dehydrofluorination process of HFO-236ea, and its amount can be reduced in a basic aqueous solution at an elevated temperature in the presence of substantially high fluoride concentration.

About 1210 lbs of HFC-236ea was fed at room temperature to an agitated reactor containing 300 lbs THF, 6 lbs tetra-n-butylammonium bromide, and 1100 lbs of 45 wt % KOH aqueous solution. After 269 lbs of HFC-236ea had been fed, the effluent was found to contain 97.0 mol % HFO-1225ye. At the end of this run, the aqueous phase solution was separated and analyzed to contain 1049 ppmw KMFA by $^{19}$F NMR. A portion of the aqueous phase solution was separated and then heated to 170° C. for one hour under autogenous pressure and KMFA was nondetectable by ICMS (i.e., having a concentration lower than 1 ppmw).

Example 3

Example 3 demonstrates that the amount of monofluoroacetate can be reduced in a basic aqueous solution at an elevated temperature in the presence of substantially high fluoride concentration.

Part of the aqueous phase solution from Example 2 was heated in an agitated vessel to 120° C. under autogenous pressure for 14 hours and then analyzed by ICMS and KMFA was nondetectable (i.e., having a concentration lower than 1 ppmw).

Example 4

Example 4 demonstrates that monofluoroacetate is generated in the dehydrofluorination process of HFC-236ea, and its amount can be reduced in a basic aqueous solution at an elevated temperature in the presence of substantially high fluoride concentration. Example 4 also demonstrates that the organic phase solutions from previous batchs of dehydrofluorination reactions can be reused in the subsequent batch of dehydrofluorination reaction.

The organic phase solution from Example 2 was reused. Another 1100 lbs of 45 wt % KOH aqueous solution was added to the organic phase solution and another 1210 lbs of HFC-236ea was added at room temperature while agitating. After 137 lbs of HFC-236ea was added, the effluent was found to contain 98.1 mol % HFO-1225ye. At the end of this run, the aqueous phase solution was separated and analyzed to contain 975 ppmw KMFA by $^{19}$F NMR. The aqueous phase solution was then heated to 165° C. for 30 minutes under autogenous pressure and the level of KMFA was found to be 8 ppmw by ICMS.

Example 5

Example 5 demonstrates that monofluoroacetate is generated in the dehydrofluorination process of HFC-245fa, and its amount can be reduced in a basic aqueous solution at an elevated temperature in the presence of substantially high fluoride concentration.

About 69 grams of HFC-245fa (purchased from Honeywell Corporation) was fed at room temperature to an agitated reactor containing THF (90 grams), Aliquat™ 336 (1.56 grams), and 45 wt % KOH aqueous solution (200 grams). After feeding 14.5 grams of HFC-245fa, the effluent was found to contain 95.4 mol % E-HFO-1234ze. At the end of the run the aqueous phase solution was separated and found to contain 1.25 ppmw of KMFA by ICMS.

The aqueous phase solution was heated to 170° C. under autogenous pressure for 6 hours and then reanalyzed by ICMS and KMFA was non-detectable (i.e., having a concentration lower than 0.5 ppmw).

What is claimed is:

1. A process for reducing the amount of monofluoroacetate in hydrofluoroolefin production, comprising:
   (a) contacting a hydrofluorocarbon with a reactant basic aqueous solution to produce an organic phase solution comprising a hydrofluoroolefin and an aqueous phase solution comprising a monofluoroacetate;
   (b) separating said aqueous phase solution from said organic phase solution; and
   (c) heating said aqueous phase solution to an effective temperature to reduce the amount of monofluoroacetate in said aqueous phase solution, wherein fluoride concentration in said aqueous phase solution is at least 0.5 wt %.

2. The process of claim 1 wherein said hydrofluorocarbon is a hydrofluoropropane and said hydrofluoroolefin is a hydrofluoropropene.

3. The process of claim 2 wherein said hydrofluoropropane is 1,1,1,2,3-pentafluoropropane and said hydrofluoropropene is 2,3,3,3-tetrafluoro-1-propene.

4. The process of claim 2 wherein said hydrofluoropropane is 1,1,1,2,3,3-hexafluoropropane and said hydrofluoropropene is 1,2,3,3,3-pentafluoro-1-propene.

5. The process of claim 2 wherein said hydrofluoropropane is 1,1,1,3,3-pentafluoropropane and said hydrofluoropropene is 1,3,3,3-tetrafluoropropene.

6. The process of claim 1 wherein said aqueous phase solution is heated to a temperature of from about 80° C. to about 300° C.

7. The process of claim 1 wherein said aqueous phase solution is heated to a temperature of from about 100° C. to about 225° C.

8. The process of claim 1 wherein said aqueous phase solution is heated to a temperature of from about 125° C. to about 200° C.

9. The process of claim 1 wherein fluoride concentration in said aqueous phase solution is at least 5 wt %.

10. The process of claim 1 wherein fluoride concentration in said aqueous phase solution is at least 12 wt %.

11. The process of claim 1 wherein the total amount of monofluoroacetate in said aqueous phase solution is reduced to less than about 10 ppmw.

12. The process of claim 1 wherein the total amount of monofluoroacetate in said aqueous phase solution is reduced to less than about 5 ppmw.

13. The process of claim 1 wherein the total amount of monofluoroacetate in said aqueous phase solution is reduced to less than about 0.5 ppmw.

14. The process of claim 1 wherein said monofluoroacetate is FCH$_2$COOK, FCH$_2$COONa, or mixtures thereof.

15. The process of claim 1 wherein said reactant basic aqueous solution is made from an inorganic base.

16. The process of claim 15 wherein said inorganic base is sodium hydroxide, potassium hydroxide, or mixtures thereof.

17. The process of claim 1 wherein said hydrofluorocarbon contacts with said reactant basic aqueous solution in the presence of a phase transfer catalyst.

18. The process of claim 17 wherein said phase transfer catalyst is methyltri-n-octylammonium chloride, tetra-n-butylammonium bromide, or mixtures thereof.

19. The process of claim 1 wherein said hydrofluorocarbon contacts with said reactant basic aqueous solution in the presence of an organic solvent.

20. The process of claim 19 wherein said organic solvent is tetrahydrofuran.

21. A process for reducing the amount of monofluoroacetate in hydrofluoroolefin production, comprising:

(a) contacting a first batch of hydrofluorocarbon with a first batch of reactant basic aqueous solution to produce a first batch of organic phase solution comprising a hydrofluoroolefin and a first batch of aqueous phase solution comprising a monofluoroacetate;
(b) separating said first batch of organic phase solution from said first batch of aqueous phase solution;
(c) mixing a second batch of hydrofluorocarbon and a second batch of reactant basic aqueous solution with said separated first batch of organic phase solution to produce a second batch of organic phase solution comprising a hydrofluoroolefin and a second batch of aqueous phase solution comprising a monofluoroacetate;
(d) combining said first batch of aqueous phase solution with said second batch of aqueous phase solution; and
(e) heating said combined aqueous phase solutions to an effective temperature to reduce the amount of monofluoroacetate in said combined aqueous phase solutions, wherein fluoride concentration in said combined aqueous phase solutions is substantially high.

22. The process of claim 21 wherein said first batch of hydrofluorocarbon is the same as said second batch of hydrofluorocarbon.

\* \* \* \* \*